United States Patent [19]

John

[11] Patent Number: 5,027,817
[45] Date of Patent: Jul. 2, 1991

[54] STATISTICAL BASED DISPLAY FOR POSITRON EMISSION TOMOGRAPHY SCANS

[75] Inventor: Erwin R. John, Mamaroneck, N.Y.

[73] Assignee: New York University, New York, N.Y.

[21] Appl. No.: 370,265

[22] Filed: Jun. 22, 1989

[51] Int. Cl.$^5$ .............................................. A61B 5/00
[52] U.S. Cl. ................................ 128/653 R; 128/654; 128/659; 250/363.03; 364/413.22
[58] Field of Search ................... 128/653 R, 659, 654; 378/901; 250/363.03; 364/413.22, 521

[56] References Cited

U.S. PATENT DOCUMENTS

| | | | |
|---|---|---|---|
| 4,532,591 | 7/1985 | Osterholm | 378/901 |
| 4,563,582 | 1/1986 | Mullani | 250/363.03 |
| 4,737,921 | 4/1988 | Goldwasser et al. | 364/521 |
| 4,772,791 | 9/1988 | Wagner, Jr. | 250/363.03 |
| 4,787,393 | 11/1988 | Fukukita | 128/660.04 |
| 4,817,433 | 4/1989 | Sato | 128/660.04 |
| 4,843,631 | 6/1989 | Steinpichler et al. | 382/17 |

OTHER PUBLICATIONS

Peled, A et al., *Digital Signal Processing*, Kreigier Publishing Co., p. 6 (1985).

Primary Examiner—Lee S. Cohen
Assistant Examiner—John D. Zele
Attorney, Agent, or Firm—Eliot S. Gerber

[57] ABSTRACT

In a medical imaging system a patient is injected with a radiopharmaceutical spontaneously emitting positrons and a PET (Positron Emission Tomography) scan is taken along parallel planes of a portion of the subject's body to produce a slice image composed of pixels arranged in a pattern. The intensity of each pixel is automatically, in a computer system, converted to digital data. The computer system then normalizes the pixels of the slice as to location by calculating the location of each pixel in an ideal or normal slice. The computer system then calculates a Z transform, on a pixel-by-pixel basis, compared to the slices from a normal group to obtain a topographic color-coded map showing the degree of abnormality at each pixel location.

15 Claims, 1 Drawing Sheet

Absolute Z-transformation

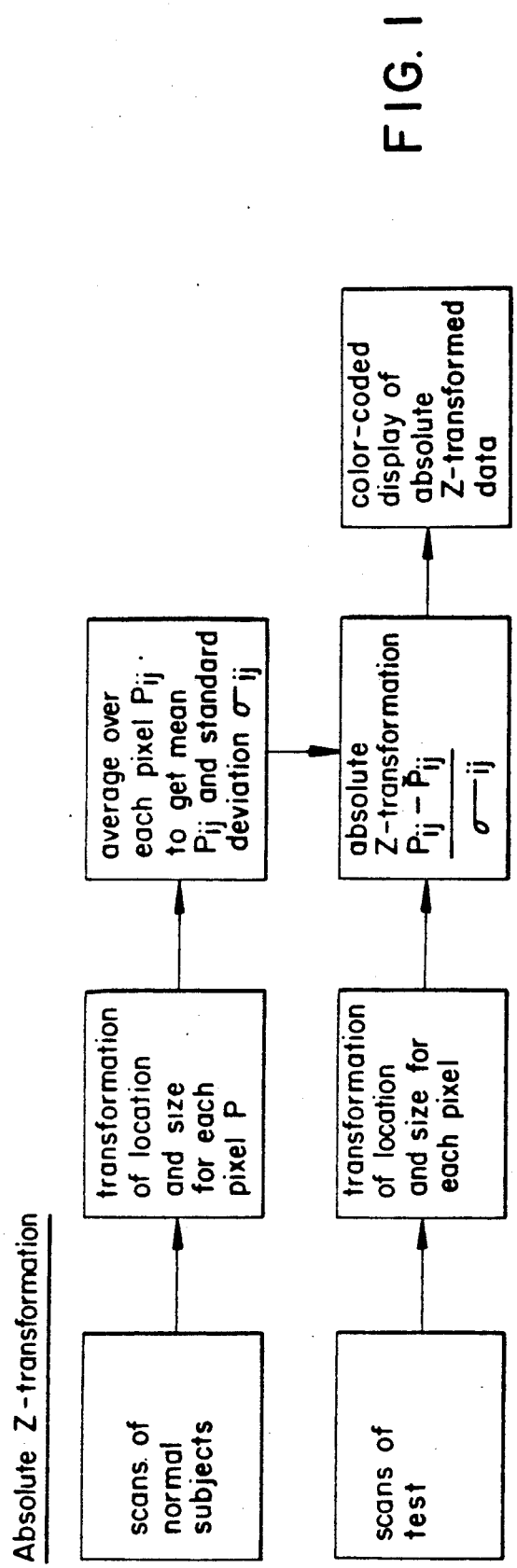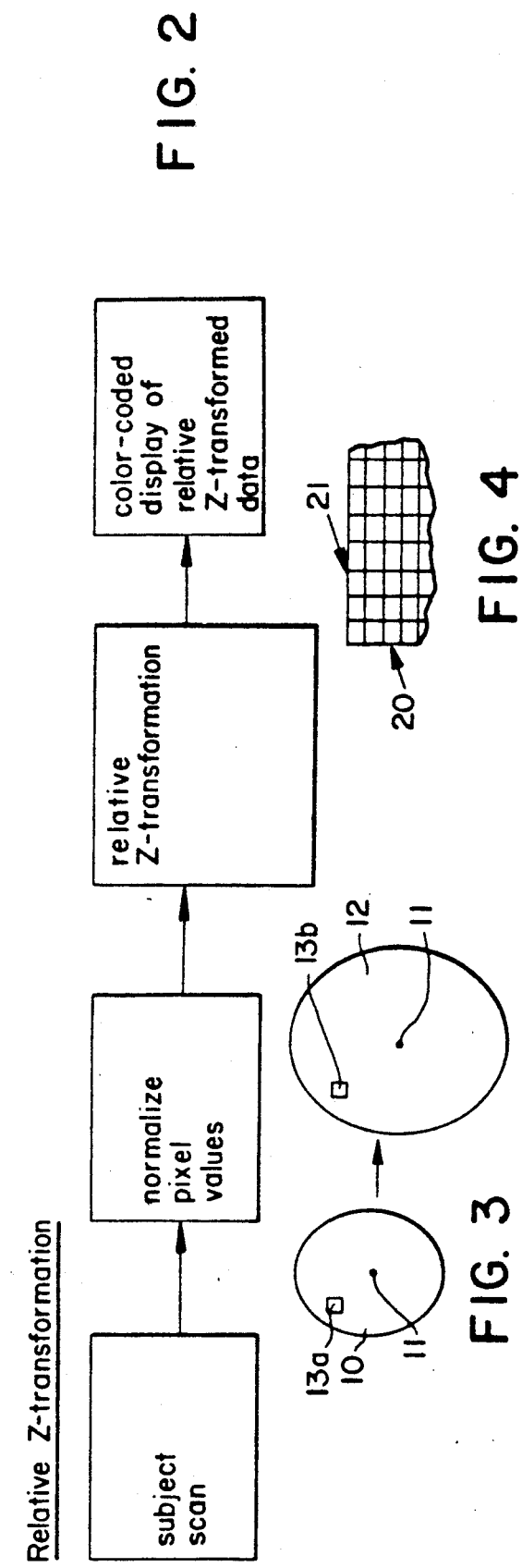

STATISTICAL BASED DISPLAY FOR POSITRON EMISSION TOMOGRAPHY SCANS

BACKGROUND OF THE INVENTION

1. Field of the Invention

The present invention relates to medical imaging systems and more particularly to Positron Emission Tomography (PET) scan systems and methods.

2. Related Art

Medical imaging systems are used in the diagnosis and treatment of patients. They are non-invasive and therefore are considered safer than surgical procedures to examine internal body tissue.

Positron Emission Tomography (PET) is an imaging technique which enables visualizing the three-dimensional distribution of radionuclides in the human body. For example, a radiopharmaceutical containing suitable short-lived cyclotron-produced radionuclides, such as carbon eleven or nitrogen thirteen in a glucose solution, is injected into the subject to determine varying metabolic rates in the different areas of the subject's brain. The subject is placed in a PET scanner. The radionuclides undergo decay with spontaneous emission of positrons. The positrons combine with a nearby electron to simultaneously generate two photons by annihilation, which travel in opposite directions along a line, i.e., anti-parallel. The two photons are detected as light flashes by two scintillation detectors positioned on opposite sides of the patient. The number of coincidences of detection (electronic collimation) by the detectors may be viewed as the degree of intensity at each pixel of images constructed by a computer system associated with the PET scanner.

Generally, the PET scanner produces a series of images corresponding to parallel planes ("slices") through a portion of the patient's body, for example, 14 slices of the brain. The physician may view the slice images, for example, to determine areas of abnormal metabolic activity.

However, the amount and accuracy of the information obtained by the physician depends upon his training, ability and attention. Some of the information content present in the PET scans may be missed, even by experienced personnel, because the image intensity variations are too slight or too gradual to be detected by eyesight, or lie within the statistical variability of the counting rate of the radioactive decay (approximately 1 $\sqrt{n}$, where n is the number of radioactive disintegrations per pixel per unit time) or lie within the normal variability encountered from individual to individual.

OBJECTIVES AND FEATURES OF THE INVENTION

It is an objective of the present invention to provide a PET scan system and method in which a patient's PET scan images may be objectively analyzed on a statistical basis.

It is a further objective of the present invention to provide a PET display which appears in shape like a portion of the patient's human body and which vividly and accurately shows regions which are abnormal and the degree of abnormality compared to a similar body portion of a normal group.

It is a further objective of the present invention to provide a PET display which shows, on an objective statistical basis, the comparison between the patient's PET scan at one time compared to a PET scan of the same body portion at a different time, treating one or a series of the scans as a self-norm for comparison purposes.

It is a further objective of the present invention to provide a PET display which more clearly delineates body areas showing abnormal activity, even though the delineation under/or the areas are too faint to be seen visually in the raw data of a PET scan image.

It is a feature of the present invention to provide a method and system for the production of a Positron Emission Tomography (PET) image display. The method includes administering a radiopharmaceutical radioactive material which spontaneously emits positrons from a patient; for example, the material may be an injected glucose solution to test metabolism. The patient is positioned in a PET scanner and at least one PET scan is taken of a body plane of the subject's body to produce a PET slice image comprising a plurality of image pixels arranged in a pattern on an image plane. The intensity of each pixel represents the positron emission from the area on the patient body plane corresponding to the pixel.

The pixel intensities are converted into subject pixel digital data representing the intensity of each pixel and that data is input to a computer system. That computer system stores normative digital data representing the slice-by-slice and pixel-by-pixel intensities of PET scans of a reference or normal sample, for example, prior scans of the patient or scans of a healthy group of subjects. The location of each pixel of each individual scan is normalized in location based on anatomical features of that subject's PET scan. The computer system automatically calculates the normalized location of each pixel in the subject's slice image based on some anatomical feature of that image and produces a pixel-by-pixel normalized-as-to-location set of subject data. The computer system then computes, on a pixel-by-pixel basis, a statistical comparison between the mean value of each pixel in the normal group and the digital value of each corresponding subject pixel, dividing by the pixel variance, to provide the degree of abnormality of the subject at each normalized-as-to-location pixel as a Z-score. The degree of abnormality of the subject at each pixel, calculated from the Z-score, is displayed in a topographic map, color-coded to reflect the significance of deviations from the normative values.

Further features of the present invention are that the administration of the radiopharmaceutical is by injection, inhalation or ingestion of a labeled substance such as a sugar solution; the PET image is of the distribution of brain neural activity showing brain region variations in the metabolic rates of sugar consumption or the uptake of the labeled substance; the degree of abnormality is expressed in standard deviation units; and the normalization of the pixels as to location is by expanding outwardly or contracting inwardly in relationship to a center point of the body portion. The labeled substance includes radioleptic drugs, radio transmitters, radioligands, precursors of metabolism, and other substances present in the brain or other body organ of interest.

SUMMARY OF THE INVENTION

In accordance with the present invention there is provided a method and system to present a statistically evaluated display which is obtained from PET scan data. A group of healthy, normal subjects provide the basis for comparison to a patient. The normal data is assembled by taking PET scan images on parallel planes (slices) with each image consisting of a portion (rows and columns) of pixels. Each normal group image and patient image is automatically, in a computer system, normalized by being transformed as to shape and size so that, in computer, each of the transformed pixels are aligned. An average and standard deviation are obtained, on a pixel-by-pixel basis, for the normal group and that average is used, in a Z transformation, which evaluates absolute intensity data on a pixel-by-pixel basis. The degree of intensity data abnormality is displayed in a topographic color-coded map of the slice. Similarly, the same method can by used to evaluate relating intensity, that is, the percentage of the total body portion utilization of any radionuclide labeled substance represented by each pixel in the image.

BRIEF DESCRIPTION OF THE DRAWINGS

Other objectives and features of the present invention will be apparent from the following detailed description, taken in conjunction with the accompanying drawings.

In the drawings:

FIG. 1 is a block flow diagram of the absolute Z transform;

FIG. 2 is a block flow diagram of the relative Z transform;

FIG. 3 illustrates the conversion of a PET scan to a normalized PET scan;

FIG. 4 illustrates the pixels in a PET scan image; and

FIG. 5 illustrates a patient in a PET scanner.

DETAILED DESCRIPTION OF THE INVENTION

Metabolic processes in the human body may be detected by injecting radiopharmaceuticals into a subject and subsequently scanning the subject with a positron emission tomographic (PET) image. The localized radiopharmaceutical spontaneously emits positrons at a rate corresponding to the local concentration of the labeled material.

The emitted positron interacts with a nearby electron, annihilating both particles to produce a pair of photons. These photons travel in anti-parallel directions (along the same line but in opposite directions) at equal velocities.

When the subject is positioned in a PET scanner, simultaneously emitted photons are detected by scintillators located on opposite sides of the subject. The detection system may be rotated around the subject or may be constructed around the subject in order to obtain sufficient data to process a tomographic image for a particular plane.

The tomographically processed data is converted to a pixel space where the data for each pixel corresponds to the total number of photons emitted from the corresponding area on the imaged plane.

The present invention describes a method for statistical evaluation of the pixelized metabolic image of a test individual or group relative to a pixelized image of the normative metabolic rate of a reference group or prior state.

The first step in this process involves the selection of subjects who will comprise the normative population. This population would exclude subjects with a history of pathology within the region of interest. Each subject would then be given a radiopharmaceutical and scanned on the PET camera. (An analogous procedure could be used to evaluate data relative to some reference state of an individual.)

In order to obtain a normative value for each pixel across this normative group of subjects, variations in slice location during imaging and variation in individual subject morphology must be normalized. This normalized assures that pixel comparison among subjects represents the same anatomical region.

The pixel pattern of the original image, as shown in FIG. 4, consists of rows 20 and columns 21 of pixels, for example, an image typically consists of 10,000 pixels.

Normalization may be performed through a transformation that relates the tomographic coordinate system to an anatomical coordinate system based on the center of mass. The distance between the center of mass and a particular pixel is related to the dimensions of a standardized body in the tomographic coordinate system by a translational, rotational and proportional transformation.

Slice normalization involves only translational transformation with a scaling factor calculated according to $$X_{tomog} = \left(\frac{X_{anat}}{T_{x\ anat}}\right)(T_{x\ tomog}) + \Delta X,$$

where $X_{tomog}$ is the total distance across all the slices of the individual subject, $X_{anat}$ is the distance across each individual slice, $T_{x\ anat}$ is the distance across each standardized slice, $T_{x\ tomog}$ is the total distance across all the slices of the standardized body of the tomograph and $\Delta X$ is the difference between the centers of mass of the two coordinate systems.

Normalization of morphology requires rotation of the imaged plane around the longitudinal axis in order to align the subject structure with the standardized structure. In addition, the coordinates of the subject pixels must be multiplied by the degree of magnification or shrinkage necessary to have a one-to-one correspondence between the pixelized image of the subject and the pixelized image of the standardized body. This transformation may be stated as:

$$Z_{tomog} = \left\{\left[\frac{Y_{anat}}{T_{Y\ anat}}\right]T_{Y\ tomog}\sin\theta + \left(\frac{Z_{anat}}{T_{Z\ anat}}\right)T_{Z\ tomog}\cos\theta + Z\right]\right\}\cdot Mag$$

$$Y_{tomog} = \left\{\left[\frac{Y_{anat}}{T_{Y\ anat}}\right]T_{Y\ tomog}\cos\theta - \left[\frac{Z_{anat}}{T_{Z\ anat}}\right]T_{Z\ tomog}\sin\theta - \Delta Y\right]\right\}Mag$$

where $\theta$ is the angle of rotation around the axis perpendicular to the plane of the slice, $T_{Y\ anat}$ is the total distance across the subject image in the Y-direction, $T_{Y\ tomog}$ is the total distance across the standardized image in the Y-direction, $T_{Z\ anat}$ is the total distance across the Z-direction of the subject image and $T_{Z\ tomog}$ is the total distance across the Z-direction of the standardized image.

As shown in FIG. 3, in a cross-section PET slice 10 of a brain, the center 11 is used to normalize the slice 10, which is small compared to the standard slice 12. The pixel location 13a of slice 10 is moved outwardly, by computer calculation, relative to center 11 to reach the normalized pixel location 13b.

After each subject's image in the normal group is normalized as to position and size, an average for the intensity of each pixel across all subjects of the normal group is found. This pixel data is the absolute means shape average of the normal group.

Next, a test group, comprised of subjects who have undergone prior pathological screening, is given a PET scan. The data for each subject is normalized to the same coordinate system as the normal group by the equations above. The "shape" normalized value for each member of the test group is then compared to the average of the normal group according to the equation:

$$Z = \frac{P_{ij} - \bar{P}_{ij}}{\sigma_{ij}}$$

where $P_{ij}$ is the shape normalized pixel value of the test subject, $\bar{P}_{ij}$ is the shape normalized average of $P_{ij}$ in the normal group and $\sigma_{ij}$ is the standard deviation of the value of $P_{ij}$ in the normal group. The resulting set of data is the absolute Z transformation that represents the probability of pathologic deviation of the test group from the norm in standard deviation units of the normal group.

The set of data obtained from the Z-transformation is then displayed on a CRT color monitor according to a color coding. Red represents significant positive Z value or deviation of increased absolute metabolic rate, green represents Z values not significantly different from zero or normal metabolic rate, and blue represents significant negative Z values or deviations of decreased absolute metabolic rate. This is the "heat scale" color code.

An example of the present invention is to determine if a patient has schizophrenia by an analysis to see if the patient has a hypometabolic pattern of sugar utilization in his cortex.

This invention also introduces the relative Z transformation into the data analysis of the individual subject's PET scan. In this transformation, each pixel value is divided by the sum of all pixel values for the subject. The relative Z transformation equation may be written:

$$Z = \frac{P_{ij} - \bar{P}_{ij}}{\frac{\sum_i \sum_j \sum_k P_{ijk}}{\sigma_{ij}}}$$

where $P_{ij}$ is the value of the particular pixel, $$\sum_i \sum_j \sum_k P_{ijK}$$

is the total of all pixel values, $\bar{P}_{ij}$ is the average pixel value as percent of total, and $\sigma_{iH}$ is the standard deviation of pixel $P_{ij}$ as percent of total activity.

The resulting data for each pixel is then displayed according to the red, green and blue color code, in which red represents the probability of higher than average relative metabolic activity, green represents average relative metabolic activity and blue represents lower than average relative metabolic activity within the particular subject image.

Modifications may be made in the above-described invention within the scope of the subjoined claims. For example, preferably the normative and subject data is corrected for age, on an age regression basis, as well as for gaussian distribution. One type of age regression system is described in *Science,* Dec. 12, 1980, Vol. 210, pgs. 1255–1258. incorporated by reference herein.

Where the statistical comparison is a Z transformation and the average value of the normal group is transformed into a gaussian distribution and the Z transformation on a pixel-by-pixel basis is given by the equation:

$$Z = (Y - \bar{Y})/\sigma$$

wherein Y is the value of the uptake in the subject of the labeled substance; $\bar{Y}$ is the average value of such uptake in the normal group after transformation to yield a gaussian distribution; and is the standard deviation of such uptake in the normal group after transformation to yield a gaussian distribution.

In addition, the computer system may analyze the normalized-as-to-location subject images by factor analysis and discriminating variables. A slice, having, for example, a 100×100 matrix providing 10,000 points, forms a vector or a series of slices, for example, 14, from vectors which are linked head-to-tail. In either case, the vectors form a factor structure in space.

The general subjects of factor analysis and discriminating variables in dealt with in a publication "Neurometric Topographic Mapping of EEG and EP Features: Application to Clinical Diagnostic and Cognitive Evaluation", John, Prichep, Freedman & Easton, in *Topographic Brain Mapping of EEG and EP,* Ed. K. Maurer, Springer-Berlin, incorporated by reference herein.

I claim:

1. A method for the production of a Positron Emission Tomography (PET) image display, including the steps, in order, of:

(a) generating a normative group of PET scans, each PET scan comprising pixel data, and, in a computer system, calculating and storing normative digital pixel data representing the means values and standard deviations of the intensities at each pixel derived from said normative group of PET scans, with each pixel of the normative digital pixel data being normalized in location based on an anatomical feature in each of the PET scans;

(b) administering a radiopharmaceutical material, which spontaneously emits positrons, to a patient;

(c) positioning the patient in a PET scan device;

(d) taking at least one PET scan on a plane of the patient's body and producing a PET slice image comprising a plurality of image pixels arranged in a pattern on an image plane with the intensity of each pixel representing the positron emission from the area on the patient body plane corresponding to the pixel;

(e) converting the pixel intensities into patient pixel digital data representing the intensity of each pixel;

(f) in said computer system, calculating the normalized location of each pixel in the patient digital pixel data based on an anatomical feature found in that image to produce a pixel-by-pixel normalized-as-to-location set of patient data;

(g) computing in said computer system, on a pixel-by-pixel basis, a statistical comparison between said normative digital pixel data and said patient pixel digital data to provide the degree of abnormality of the patient at each normalized as-to-location pixel compared to said normative group; and (h) displaying in a color-coded topography map display the degree of abnormality of the patient at each pixel.

2. A method as in claim 1 wherein the administration of the radiopharmaceutical is by injection of a material selected from the radioactive substance group consisting of a radioactively labeled sugar solution, radioleptic drugs and radioligands; the PET image is of the distribution of brain neural activity showing brain region variations; and the degree of abnormality is expressed in standard deviation units of the normative group.

3. A method as in claim 2 wherein the patient may have schizophrenia and the analysis is to determine if the patient has a hypometabolic pattern of sugar utilization in the cortex and the map is of the cortex of the patient.

4. A method as in claim 2 wherein the statistical comparison is a Z transformation and the average value of the normative group is transformed into a gaussian distribution and the Z transformation on a pixel-by-pixel basis is given by the equation:

$$][Z=(Y=Y)/\sigma]Z=(Y-\bar{Y})/\sigma$$

wherein Y is the value of the uptake in the patient of the labeled substance, $\bar{Y}$ is the average value of said uptake in the normal group after transformation to yield a gaussian distribution, and $\sigma$ is the standard deviation of said uptake in the normal group after transformation to yield a gaussian distribution.

5. A method as in claim 1 wherein in step (f), the normalization of the pixels as to location is by mathematically expanding outwardly or contracting inwardly in relationship to a center point in the image of the patient.

6. A method as in claim 5 wherein the center point is found in relationship to the brain of the patient.

7. A method as in claim 1 in which said color coded map red represents positive abnormality, green represents zero abnormality and blue represents negative abnormality.

8. A method as in claim 1 wherein the normative group of PET scans are generated from a group of healthy normal subjects.

9. A method as in claim 1 wherein the normative group of PET scans are generated from the same patient at a different time.

10. A method as in claim 1 wherein said statistical comparison is a Z transform on a pixel-by-pixel basis given by the equation $$Z = \frac{P_{ij} - \bar{P}_{ij}}{\sigma_{ij}}$$

where $P_{ij}$ is the normalized as-to-location pixel value of the patient data; $\bar{P}_{ij}$ is the normalized as-to-location average of the normative group and $\sigma$ is the standard deviation of the normalized group.

11. A method as in claim 1 wherein the patient pixel digital data represents the absolute intensity of each pixel.

12. A method as in claim 1 wherein the patient pixel digital data represents the relative intensity of each pixel compared to the average intensity of the pixels.

13. A system for medical imaging including:
(a) a Positron Emission Tomography (PET) scan means for producing an image of a body portion of a patient administered with a radiopharmaceutical material which spontaneously emits positrons by taking at least one PET scan on a plane of a portion of the patient's body, said image comprising a plurality of image pixels arranged in a pattern with the intensity of each pixel representing the positron emission from a corresponding area on the body plane;
(b) means for converting the pixel intensities into patient pixel digital data;
(c) normalizing computer means for automatically computing the normal location of each pixel of the patient pixel digital data based on an anatomical feature of the PET patient pixel image to produce a set of normalized patient pixel digital data based upon said patient digital data which represents a normalized pixel pattern;
(d) Z transform computer means, including computer memory, for automatically computing on a slice-by-slice and pixel-by-pixel basis, a Z transformation statistical comparison of said normalized patient digital data with a set of normative data stored in said computer memory to provide the degree of abnormality of the subject at each normalized pixel; and
(e) means for displaying a color-coded topographic map showing the degree of abnormality of the patient at each pixel.

14. A system as in claim 13 wherein said means of displaying the map shows the degree of abnormality expressed in standard deviation units of a reference sample.

15. A system as in claim 13 wherein the normalized pixel pattern is based upon the size and shape of the patient body portion and in which the normalizing computer means includes means to calculate the pixels either mathematically expanded outwardly or contracted inwardly in relationship to a center point in the image of the body portion.

* * * * *